US010105701B2

(12) United States Patent
Ledden et al.

(10) Patent No.: US 10,105,701 B2
(45) Date of Patent: Oct. 23, 2018

(54) MICROFLUIDIC DISTRIBUTING DEVICE

(71) Applicant: Siemens Healthcare Diagnostics Inc., Tarrytown, NY (US)

(72) Inventors: David J. Ledden, Medway, MA (US); Dafeng Chen, Sharon, MA (US); James E. Rasmussen, Plainville, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 82 days.

(21) Appl. No.: 15/206,669

(22) Filed: Jul. 11, 2016

(65) Prior Publication Data

US 2016/0318019 A1    Nov. 3, 2016

Related U.S. Application Data

(63) Continuation of application No. 14/776,172, filed as application No. PCT/US2014/025753 on Mar. 13, 2014, now Pat. No. 9,416,776.
(Continued)

(51) Int. Cl.
*B01L 3/00* (2006.01)
*B01L 3/02* (2006.01)
(Continued)

(52) U.S. Cl.
CPC ... *B01L 3/502753* (2013.01); *B01L 3/502715* (2013.01); *B01L 3/502738* (2013.01); *G01N 1/30* (2013.01); *B01L 2200/0605* (2013.01); *B01L 2200/14* (2013.01); *B01L 2200/142* (2013.01); *B01L 2200/16* (2013.01); *B01L 2300/0645* (2013.01); *B01L 2300/087* (2013.01); *B01L 2300/0816* (2013.01); *B01L 2300/0864* (2013.01); *B01L 2300/0887* (2013.01); *B01L 2300/161* (2013.01); *B01L 2400/0688* (2013.01); *B01L 2400/084* (2013.01)

(58) Field of Classification Search
CPC .. B01L 3/00; B01L 3/02; G01N 33/00; G01N 15/06; G01N 33/48
USPC .......... 422/50, 68.1, 63, 64, 65, 81, 82, 502, 422/503, 504, 509; 436/43, 174, 180; 435/283.1
See application file for complete search history.

(56) References Cited

U.S. PATENT DOCUMENTS 6,066,448 A   5/2000  Wohlstadter et al.
6,296,126 B1  10/2001 Peters
(Continued)

FOREIGN PATENT DOCUMENTS

CN   102822680 A   12/2012
WO   2008052168 A2  5/2008

OTHER PUBLICATIONS

European Search Report and Written Opinion of European Application No. 14769287.5 dated Dec. 2, 2016.
(Continued)

*Primary Examiner* — Brian J. Sines
(74) *Attorney, Agent, or Firm* — Kyle D. Petaja (57) ABSTRACT

A microfluidic distributing device having a plurality of microchannels for the analysis of a fluid sample (such as blood). The microfluidic distributing device has a fluid sample entry port from which subsamples of the fluid sample are distributed to the plurality of microchannels in which fluid subsamples are treated for analysis by test devices.

8 Claims, 7 Drawing Sheets

Related U.S. Application Data (60) Provisional application No. 61/790,580, filed on Mar. 15, 2013.

(51) Int. Cl.
- *G01N 33/00* (2006.01)
- *G01N 15/06* (2006.01)
- *G01N 33/48* (2006.01)
- *G01N 1/30* (2006.01)

(56) References Cited

U.S. PATENT DOCUMENTS

| | | | |
|---|---|---|---|
| 6,632,404 | B1 | 10/2003 | Freitag et al. |
| 7,459,127 | B2 | 12/2008 | Pugia et al. |
| 8,133,671 | B2 | 3/2012 | Williams et al. |
| 8,822,167 | B2 | 9/2014 | Burd et al. |
| 9,221,047 | B2 | 12/2015 | Ferraro et al. |
| 2002/0153046 | A1* | 10/2002 | Dantsker .......... B01L 3/502738 137/833 |
| 2002/0166592 | A1 | 11/2002 | Liu et al. |
| 2002/0185183 | A1* | 12/2002 | O'Connor .......... B01F 5/064 137/814 |
| 2004/0142411 | A1* | 7/2004 | Kirk .......... B01L 3/5025 435/33 |
| 2004/0238052 | A1* | 12/2004 | Karp .......... B01F 5/0471 137/822 |
| 2004/0262223 | A1 | 12/2004 | Strook et al. |
| 2005/0013732 | A1 | 1/2005 | Battrell et al. |
| 2005/0041525 | A1 | 2/2005 | Pugia et al. |
| 2005/0069459 | A1 | 3/2005 | Ahn et al. |
| 2005/0176135 | A1 | 8/2005 | Jones |
| 2008/0014576 | A1 | 1/2008 | Jovanovich et al. |
| 2008/0085551 | A1 | 4/2008 | Kim et al. |
| 2008/0135502 | A1 | 6/2008 | Pyo et al. |
| 2009/0036668 | A1 | 2/2009 | Elizarov et al. |
| 2009/0246866 | A1 | 10/2009 | Naser et al. |
| 2009/0283452 | A1 | 11/2009 | Lean et al. |
| 2009/0317798 | A1 | 12/2009 | Heid et al. |
| 2011/0236264 | A1* | 9/2011 | Rajagopal .......... B01L 3/502753 422/82.07 |
| 2015/0024436 | A1 | 1/2015 | Eberhart et al. |
| 2017/0307599 | A1* | 10/2017 | Deane .......... G01N 33/5094 |

OTHER PUBLICATIONS

Michael J. Felton, "The New Generation of Microvalves", Oct. 1, 2003, Analytical Chemistry, pp. 429A-432A.

Stefan Haeberle et al., "Centrifugal Extraction of Plasma from Whole Blood on a Rotating Disk", 2006, The Royal Society of Chemistry, Lab on a Chip, vol. 6, pp. 776-781.

Sung Yang et al., "A Microfluidic Device for Continuous, Real Time Blood Plasma Separation", 2006, The Royal Society of Chemistry, Lab on a Chip, vol. 6, pp. 871-880.

Virginia VanDelinder et al., "Separation of Plasma from Whole Human Blood in a Continuous Cross-Flow in a Molded Microfluidic Device", Jun. 1, 2006, Analytical Chemistry, vol. 78, No. 11, pp. 3765-3771.

Jimmie B. Vaught, "Blood Collection, Shipment, Processing and Storage", Cancer Epidemiology Biomarkers & Prevention, Sep. 2006, vol. 15, pp. 1-6.

Katherine Bourzac, "Ten-Minute Blood Test", Nov. 17, 2008, MIT—Technology Review, pp. 1-2.

Rong Fan et al., "Integrated Barcode Chips for Rapid, Multiplexed Analysis of Proteins in Microliter Quantities of Blood", Dec. 2008, Nature Biotechnology, vol. 26, No. 12, pp. 1373-1378.

Ivan K. Dimov et al., "Self-Powered Integrated Microfluidic Blood Analysis System (SIMBAS)", Nov. 2009, Thirteenth International Conference on Miniaturized Systems for Chemistry and Life Sciences, pp. 384-386.

Ivan K. Dimov et al., Self-Contained, Self-Powered Integrated Microfluidic Blood Analysis System (SIMBAS), 2010, The Royal Society of Chemistry, Lab on a Chip, pp. 1-4.

Marilynn Marchione, "Blood Test for Cancer with Microchip is Super-Sensitive, More Informative, Researchers Say", Jan. 3, 2011, Associated Press, pp. 1-4.

Sara Yang, "New Blood Analysis Chip Could Lead to Disease Diagnosis in Minutes", Mar. 16, 2011, Berkeley News, pp. 1-2.

Rebecca Hersher, "Microfluidic Chips Promise Better Diagnosis for Sickle Cell Disease", Apr. 20125, Nature Medicine, vol. 18, No. 4, p. 475.

International Search Report and Written Opinion of International Application No. PCT/US2014/025753 dated Jul. 10, 2014.

* cited by examiner

MICROFLUIDIC DISTRIBUTING DEVICE

The present application is a continuation of U.S. application Ser. No. 14/776,172, filed Sep. 14, 2015 which claims the benefit of International Application No. PCT/US2014/025753, filed Mar. 13, 2014 which claims the benefit of U.S. Provisional Application No. 61/790,580, filed Mar. 15, 2013. All of the applications are incorporated by reference herein in their entirety.

BACKGROUND OF THE INVENTIVE CONCEPTS

1. Field of the Inventive Concepts

The inventive concepts disclosed and claimed herein generally relate to microfluidic devices which have a plurality of channels for distributing portions of a fluid sample for analysis.

2. Brief Description of Related Art

Analysis of fluid samples is important in medical applications, such as the diagnosis of many diseases. In particular, the collection, processing, and analysis of blood specimens are a crucial aspect of many medical diagnoses for determining treatment options. Conventional blood analysis processes require that several sample tubes need to be drawn from the patient depending on the types of tests required (e.g., some assays require EDTA-treated plasma, heparin-treated plasma or whole blood). Commonly, the multiple blood samples are taken using color-coded blood collecting tubes so that the blood samples can be treated with the variety of different additives (reagents) therein for being subjected to different testing protocols. After being drawn the samples generally need to be centrifuged to separate the cells from the plasma. The correct sample types then need to be placed on an instrument for the desired assays.

Blood is a complex mixture of suspended cellular components (erythrocytes, leukocytes, and thrombocytes) and dissolved substances (e.g., electrolytes, proteins, lipids, carbohydrates, and amino acids). If blood is withdrawn from a vein and placed in a plain, untreated test tube, the blood will clot. Blood specimens of this type are used to harvest blood serum for testing. If a fresh blood specimen is promptly mixed with an anticoagulant (e.g., oxalates, citrates, ethylene diamine tetraacetates, heparins), the whole blood will remain fluid, allowing the cells to remain homogenously suspended in the blood plasma. If the anticoagulated whole blood specimen is allowed to stand for a sufficient length of time or the specimen is centrifuged, the cells will sediment to the bottom of the test tube, leaving a supernatant fluid called blood plasma. The principle difference between serum and plasma is that serum contains no fibrinogen. The fibrinogen is consumed in its conversion to an insoluble fibrin matrix which traps the cells and forms the clot. Therefore, an important early decision in blood collection (Vaught, J. B., "Blood Collection, Shipment, Processing, and Storage" *Cancer Epidemiol Biomarkers Prev.* Sep. 2006 15:1582) is whether to collect anticoagulated blood (consisting of plasma, buffy coat, and red blood cells (RBCs)) or coagulated blood (consisting of serum and clotted RBCs).

There are several types of anticoagulants, which differ in their mechanisms of action and which need to be chosen carefully to avoid problems with certain laboratory applications. Heparin, for example, binds to and accelerates the inactivation of thrombin and other clotting factors. EDTA chelates metals, such as calcium and magnesium, which may be beneficial for some blood-based assays but which adversely affect others. As an anticoagulant, EDTA is well suited for DNA-based assays but is problematic for cytogenetic analysis. Despite anecdotal accounts of problems in PCR assays, studies have generally found that the use of heparin or EDTA produces equivalent results in PCR assays. Acid citrate dextrose (ACD) also chelates calcium. Citrate-stabilized blood results in better quality RNA and DNA than other anticoagulants and yields more lymphocytes for culture. However, in liquid form, acid citrate dextrose dilutes plasma, and a dilution factor will have to be considered when calculating assay results. If variable volumes of blood are drawn from study participants, dilution can result in erroneous results if volumes are not carefully recorded.

Other special collection tubes, such as serum separator tubes and CELL PREPARATION TUBES (Becton Dickinson), allow for more convenient separation of blood fractions. However, the serum separator tubes have been found to affect some assays, such as thyroxin and cortisol. Special collection tubes with protease inhibitors have been developed, which preserve proteins for proteomics analyses. The analysis of trace metals in blood also requires caution, as trace metals may be present in the evacuated collection tubes.

Although collection of multiple samples into multiple containers is the current state of the art in blood collection, such multiple sample collection is not only inconvenient for the subject who must provide the blood samples, but it also introduces potential for processing errors by loss or mislabeling of tubes, and variation in tube and/or reagent quality leading to spurious laboratory results. Furthermore, it is often difficult to obtain a sufficient amount of blood from a particular subject to dispose into the tube. Small, capillary tube samples are generally easier to obtain. A need exists for a device and method which allows for a more efficient treatment and analysis of fluid samples, such as blood samples, taken from a subject. It is to such a device and method that the inventive concepts disclosed and claimed herein are directed.

SUMMARY OF THE INVENTIVE CONCEPTS

The inventive concepts disclosed and claimed herein generally relate to using a microfluidic distributing device containing one or more of microchannels, valves, mixing chambers, separation structures, and metering components for separating, distributing and treating, and then analyzing, fluid samples, particularly blood samples. Such microfluidic device design may allow for selective capture of blood cells and/or components, and/or plasma components, reaction of captured cells and plasma components, with detection reagents, and capture and/or isolation of blood cells and/or components, for example.

The presently claimed and disclosed inventive concepts relate to microfluidic analysis devices and systems adapted to apportion, distribute, treat and optionally analyze small fluid samples of, for example, 0.1 to 20 µL, thereby making possible accurate and repeatable assays of the analytes of interest in such samples. In one embodiment the microfluidic device is designed for analysis of blood. The devices have one or more microfluidic analysis units each comprising a microchannel in fluid communication with an entry port which provides access for a small sample of fluid and for apportionment and distribution of the sample to a plurality of reagent mixing areas. Each reagent mixing area has a microchannel leading to an outlet port which can be aligned to a test device for analyzing the treated sample.

The microfluidic device of the presently claimed and disclosed inventive concepts may include one or more overflow chambers, reaction chambers, microconduits with capillary stops, and air vents. The capillary stops, when present, direct the fluid flow in a preferred direction.

In one aspect, the presently claimed and disclosed inventive concepts include a method of supplying a liquid sample to a microfluidic analysis device in which liquid is introduced to a sample entry port, where from it flows through a microchannel by capillary forces or by other methods of passive or active propulsion into a reagent area (reaction chamber) where the liquid sample is exposed to and mixed with a reagent. In some aspects, the microchannels have capillary stops which comprise, for example, narrow passageways for directing flow of the fluid in the microchannel.

In one aspect, the presently claimed and disclosed inventive concepts include a kit for a sample collection device comprising the microfluidic distributing device and one or more test devices for analyzing the fluid sample treated in the microfluidic distributing device. The microchannels may be rendered selective as adhesion can be adjusted for a cell type or cell components In another aspect, the inventive concepts disclosed and claimed herein relate to using a microfluidic distributing device to treat and analyze a single whole blood sample. The blood sample is supplied to an entry port of the microfluidic distributing device. The sample is routed (generally via active fluidics) to an area on the device to generate the appropriate sample types(s) for the assays requested. The processed samples then are routed to the desired test devices (e.g., test cartridges or test cards) for analysis and evaluation. The invention, in one embodiment, eliminates centrifugation of whole blood sample to generate plasma(s), whole blood, or hemolyzed blood by using active fluidics, chemicals and membranes (or other cell separation technique). A single whole blood sample is placed on the microfluidic distributing device that would, via valves and microchannels, route the sample to form the appropriate sample types (processing) and to the test cartridge(s) for the assay(s) ordered. The presently disclosed and claimed inventive concepts speed up sample processing and assay throughput. The microfluidic distributing device generally interfaces with several test devices (test cartridges, test cards, or test modules) or can be integrated into individual analyte specific test devices. Additional microfluidic distributing devices may be fluidly connected to one another in sequential processing.

The inventive concepts disclosed and claimed herein also relate to uses of microfluidic distributing devices and one or more test devices in a kit or system for analyzing a treated portion of the fluid sample applied to the microfluidic distributing device. Other objectives of the presently disclosed and claimed inventive concepts will become apparent upon a reading of the description supplied below.

BRIEF DESCRIPTION OF THE DRAWINGS

To assist those of ordinary skill in the relevant art in making and using the subject matter hereof, reference is made to the appended drawings and schematics, which are not intended to be drawn to scale, and in which like reference numerals are intended to refer to similar elements for consistency. For purposes of clarity, not every component may be labeled in every drawing. Certain features and certain views of the figures may be shown exaggerated and scale or in schematic in the interest of clarity and conciseness. In the drawings.

DETAILED DESCRIPTION OF EXEMPLARY EMBODIMENTS

Before explaining the at least one non-limiting embodiment of the inventive concepts disclosed herein in detail, it is to be understood that the inventive concepts are not limited in its application to the details of construction, experiments, exemplary data, and/or the arrangement of the components set forth in the following description, or illustrated in the drawings. The presently disclosed and claimed inventive concepts are capable of other embodiments or of being practiced or carried out in various ways. Also, it is to be understood that the phraseology and terminology employed herein is for purpose of description only and should not be regarded as limiting in any way unless specifically indicated as such.

In the following detailed description of embodiments of the presently disclosed inventive concepts, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the present disclosure.

Unless defined otherwise, all technical and scientific terms used herein have the same meanings as commonly understood by one skilled in the art to which the presently claimed and disclosed inventive concepts pertain. For example, the term "plurality" refers to "two or more." The singular forms "a," "an," and "the" include plural referents unless the context clearly indicates otherwise. Thus, for example, reference to "a reaction chamber" refers to 1 or more, 2 or more, 3 or more, 4 or more or greater numbers of reaction chambers. The term "about", where used herein when referring to a measurable value such as an amount, a temporal duration, and the like, is meant to encompass variations of ±20% or ±10%, or ±5%, or ±1%, or ±0.1% from the specified value, as such variations are appropriate to perform the disclosed methods and as understood by persons having ordinary skill in the art.

Further, unless expressly stated to the contrary, "or" is intended to be inclusive and not an exclusive. For example, "A or B" may refer to either A or B, or both A and B; that is, the statement "X may enter A or B" indicates that X may enter A, or B, or both A and B, unless indicated otherwise.

As used herein, the term "reagent" refers to any element, compound, ion, or molecule with which any portion of the fluid sample, or complex derived from the fluid sample, may react, for example to form a detectable signal. The reagents may be, but are not limited to, indicator dyes, metals, polymers, enzymes, proteins, peptides, nucleic acids, nucleotides, saccharides, lipids, antibodies, electrochemically-reactive substances, chemicals, radioactive elements or compounds, labels, or other analytes known to persons having ordinary skill in the art. The reagents may be placed on or incorporated into carriers (substrates) such as papers, membranes, polymers, or other carriers known in the art. The reagents may be dry, or wet. More than one reagent may be placed on a carrier. Typical chemical reactions which involve the reagents include, but are not limited to, dye binding, enzymatic, immunologic, oxidation or reduction chemistries.

As used herein, the term "affinity reagent" and any variations thereof, is intended to comprise reagents such as antibodies and other binding molecules, used to attract and retain specific cell types. As will be understood by persons of ordinary skill in the art, affinity reagents are typically, but not necessarily, attached to a surface or may attract and retain one or more cells to a surface.

As used herein, the term "detection reagent" and any variations thereof comprises one or more of a first molecule or cell (such as a peptide, an antibody, a nucleic acid, and combinations thereof, for example), which first molecule binds to a second target molecule or cell in order to identify or track such second target molecule or cell. As will be understood by persons of ordinary skill in the art, a detection agent is typically, but not necessarily, unattached to a surface. Further, the same or similar molecules may function as a detection reagent when not attached to a surface, and as an affinity reagent when attached, deposited on, or otherwise connected with, a surface. Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

In at least one embodiment, the reagent used in the microfluidic distributing device is at least one lyophilized reagent. The lyophilized reagent comprises, for example, at least one of a salt, a protein, and a catalyst. The lyophilized reagent may be disposed in any form, such as but not limited to, a bead or a hemisphere. The composition may be maintained in a substantially air tight environment until use thereof. In certain embodiments, the lyophilized reagent may include salt(s), protein(s) and/or catalyst(s). Examples of compositions that may be present in the lyophilized reagent utilized in accordance with the presently disclosed and claimed inventive concept(s) include, but are not limited to, sodium, potassium, calcium, and/or chlorine salts (such as but not limited to, calcium chloride, lithium chloride, sodium bicarbonate, sodium citrate, sodium sulfite, and/or sodium sulfate), glucose oxidase, glucose dehydrogenase, hexokinase, glucose dehydrogenase, hexokinase, lactate oxidase, hemoglobin, cobalt, and combinations thereof.

The microfluidic distributing device may be equipped with a microprocessor chip and microcircuitry for controlling one or more aspects of operation of the device such as the opening and closing of valves and/or the active pumping of fluids. The microprocessor may be programmed with a code which identifies one or more of the patient, the fluid sample, reagents in the device, or instructions for analysis of the fluid, for example.

The volume of the fluid sample which the microfluidic distributing device can receive can vary widely, for example between about 10 µL to about 1200 µL, and is usually in a range from about 10 µL to about 40 µL. The sample volumes which the fluid sample is apportioned into can vary, but typically, such samples have volumes of about 1 µL to 20 µL per reagent, although they may range from 0.1 µL to 200 µL per reagent, for example, depending on the type of fluid sample and the number of portions into which the fluid sample is separated.

The microfluidic distributing device, in non-limiting embodiments, may be made of plastics such as polycarbonate, polystyrene, polyacrylates, or polyurethane, alternatively or in addition to, they can be made from silicates, and/or glass. When moisture absorption by the plastic is not a substantial concern, the plastics preferably used may include, but are not limited to, ABS, acetals, acrylics, acrylonitrile, cellulose acetate, ethyl cellulose, alkylvinylalcohols, polyaryletherketones, polyetheretherketones, polyetherketones, melamine formaldehyde, phenolic formaldehyde, polyamides (e.g., nylon 6, nylon 66, nylon 12), polyamide-imide, polydicyclopentadiene, polyether-imides, polyethersulfones, polyimides, polyphenyleneoxides, polyphthalamide, methylmethacrylate, polyurethanes, polysulfones, polyethersulfones and vinyl formal. When moisture absorption is of concern, preferably the plastics used to make the chip include, but are not limited to: polystyrene, polypropylene, polybutadiene, polybutylene, epoxies, Teflon™, PET, PTFE and chloro-fluoroethylenes, polyvinylidene fluoride, PE-TFE, PE-CTFE, liquid crystal polymers, Mylar®, polyester, LDPE, HDPE, polymethylpentene, polyphenylene sulfide, polyolefins, PVC, and chlorinated PVC.

It should be understood that the various components of the presently disclosed and claimed invention can be provided as kits containing various combinations of the components described herein that can be assembled or used by the user and/or patient in the manners disclosed above.

In one embodiment, the principle of operation of the system of the presently claimed and disclosed inventive concepts is that the sample is provided to a reagent in a reagent area (reaction chamber) through the use of a unidirectional hydrophilic capillary flow principle where the sample flows from a sample entry port, through the reaction chamber, towards an exit port. The microfluidic distributing device may have a vent which is open to air during flow of the fluid sample. The microfluidic distributing device may have active or passive valves for controlling flow, stopping, advancing, or inhibiting "backflow" of the subsamples therein (as explained below for example).

Described herein, and shown in the accompanying figures, are several non-limiting embodiments of microfluidic distributing devices and sample analysis systems of the presently claimed and disclosed inventive concepts which may be used for analyzing a fluid sample according to the presently claimed and disclosed inventive concepts. The fluid sample is generally from a biological source. A "liquid"

refers to any substance in a fluid state having no fixed shape but a substantially fixed volume.

The microfluidic distributing devices of the presently claimed and disclosed inventive concepts typically use smaller channels (referred to herein as microchannels or microconduits) than have been used by previous workers in the field. In particular, the microchannels (microconduits) used in the presently claimed and disclosed inventive concept(s) typically have widths in the range of about 5 µm to 1000 µm, such as about 10 µm to 500 µm, whereas channels an order of magnitude larger have typically been used by others when capillary forces are used to move fluids. Depths of the microchannels are typically in a range of 5 µm to 100 µm. The minimum dimension for the microchannels is generally about 5 µm, unless it is desired to use smaller channels to filter out components in the sample being analyzed. It is also possible to control movement of the samples in the microchannels by treating the microchannels to become either hydrophilic or hydrophobic depending on whether fluid movement is desired or not. The resistance to movement can be overcome by a pressure difference, for example, by applying pumping, vacuum, electroosmosis, heating, or additional capillary force. As a result, liquids can move from one region of the device to another as required for the analysis being carried out.

The microfluidic distributing devices of the presently claimed and disclosed inventive concepts, also referred to herein as "chips" or "microfluidic chips", are generally small and flat, typically, but not limited to, about 0.5 to 2 square inches (12.5 to 50 mm$^2$) or disks having, but not limited to, a radius of about 15 to 60 mm. The volume of apportioned fluid sample introduced into a particular microfluidic circuit will be small. By way of non-limiting example, the sample typically will contain only about 0.1 to 10 µL for each assay, although the total volume of a specimen may range from 10 to 200 µL. In one embodiment, the microfluidic distributing device of the presently claimed and disclosed inventive concepts comprises a square or rectangular strip or card, or disk. The microfluidic distributing devices (chips) used in the presently claimed and disclosed inventive concepts generally are intended to be disposable after a single use. Generally, disposable chips will be made of inexpensive materials to the extent possible, while being compatible with the reagents and the samples which are to be analyzed.

The microchannels of the microfluidic distributing devices described herein typically are hydrophilic, which in one embodiment is defined with respect to the contact angle formed at a solid surface by a liquid sample or reagent. Typically, a surface is considered hydrophilic if the contact angle is less than 90° and hydrophobic if the contact angle is greater than 90°. Plasma induced polymerization may be carried out at the surface of the passageways. The microfluidic distributing devices of the presently claimed and disclosed inventive concepts may also be made with other methods used to control the surface energy of the capillary (microchannel) walls, such as coating with hydrophilic or hydrophobic materials, grafting, or corona treatments. The surface energy of the capillary walls may be adjusted, i.e., the degree of hydrophilicity or hydrophobicity, for use with the intended sample fluid, for example, to prevent deposits on the walls of a hydrophobic passageway or to assure that none of the liquid is left in a passageway. For most passageways in the presently claimed and disclosed inventive concepts, the surface is generally hydrophilic since the liquid tends to wet the surface and the surface tension force causes the liquid to flow in the passageway. For example, the surface energy of capillary passageways can be adjusted by known methods so that the contact angle of water is between 10° to 60° when the passageway is to contact whole blood or a contact angle of 25° to 80° when the passageway is to contact urine.

Movement of liquids through the microchannels, in one embodiment, may be controlled or directed by capillary stops, which, as the name suggests, stop liquids from flowing through the capillary by a change in capillary forces. For example, a more narrow capillary width can have a stronger stop strength than a less narrow capillary, thereby causing the fluid to move through the less narrow capillary in preference of movement through the more narrow capillary. Fluid flow in the devices of the presently claimed and disclosed inventive concepts may be initiated by capillary forces driven by atmospheric pressure although in some embodiments flow may be initiated or reinitiated by other external or active forces such as automatic pumps as discussed elsewhere herein. Thus while not required in preferred embodiments of the presently claimed and disclosed inventive concepts, it may be convenient in some instances to continue applying force while liquid flows through the capillary passageways in order to facilitate analysis.

Since a fluid sample may be introduced into the microfluidic distributing device in several ways, the actual shape of the opening in the sample entry port may vary. The shape of the opening is not considered to be critical to the performance, since several shapes may be satisfactory. For example, it may be merely a circular opening into which the sample is placed. Alternatively, the opening may be tapered to engage a corresponding shape in a pipette, capillary, or outlet which deposits the sample. Such ports may be sealed closed so that nothing can enter the microfluidic chip until the port is engaged by the device holding the sample fluid, such as a syringe or pipette. Depending on the carrier type, the sample may be introduced by a positive pressure, as when a plunger is used to force the sample into the entry port. Alternatively, the sample may be merely placed at the opening of the entry port and capillary action used and atmospheric pressure to pull or push the sample into the microfluidic distributing device. Excess sample is preferably not to be left on a surface however, since cross-contamination may occur. Also, in alternate embodiments, the sample may be placed at the opening of the entry port and a vacuum used to pull the sample into the microfluidic chip. As has already been discussed, when the opening is small, sufficient capillary forces are created by the interaction of the passage walls and the surface tension of the liquid. Typically, biological samples contain water and the walls of the entry port and associated passageways will be hydrophilic so that the sample will be drawn into the microfluidic chip even in the absence of added pressure.

The microfluidic distributing device in certain embodiments contains mechanisms or means for separating cellular components from the plasma. For example, a separation area may contain membranes or glass fibers for separating red blood cells from plasma so that they do not interfere with the analysis of plasma. One or more blood anti-coagulants (e.g., heparin, EDTA, oxalates, sodium citrate, acid citrate dextrose, and sodium fluoride/potassium-oxalate) may be included in the microchannel, reagent area, or elsewhere to prevent coagulation, and hemolytic reagents may be included to cause lysis of cells.

Any one of the chambers or microchannels of the microfluidic distributing device may comprise microstructures known in the art which are used to assure uniform contact and mixing of the liquid sample with a reagent or other agent which has been disposed in the reagent area or in the microchannel. In some cases the reagents are liquids which have been coated on a porous support and dried. For example, the microstructures may comprise an array of posts disposed in a reagent area so that the liquid sample must pass from the entry port in a non-linear, non-direct, direction. The liquid is constantly forced to change direction as it passes through the array of posts. Each of the posts may contain one or more wedge-shaped cutouts which facilitate the movement of the liquid as discussed in U.S. Pat. No. 6,296,126, for example.

Other types of microstructures which are useful are known to persons having ordinary skill in the art and include (but are not limited to) three dimensional post shapes with cross-sectional shapes that can be circles, stars, triangles, squares, pentagons, octagons, hexagons, heptagons, ellipses, crosses or rectangles or combinations thereof. Microstructures with two-dimensional shapes such as a ramp leading up to reagents on plateaus may also be useful.

Microfluidic distributing devices of the presently claimed and disclosed inventive concepts have many applications. Analyses may be carried out on samples of many fluids of biological origin which are fluids or have been fluidized including, but not limited to, blood, plasma, serum, urine, bladder wash, saliva, sputum, spinal fluid, intestinal fluid, intraperitoneal fluid, food, cystic fluids, ascites, sweat, tears, feces, semen, nipple aspirates, and pus. As noted above, blood is of particular interest. Also included are processed biological fluids such as milk, juices, wines, beer, and liquors. Fluids of non-biological origin or which may be contaminated, such as water, are also included. A sample of the fluid to be tested is deposited in the entry port of the microfluidic distributing device and subsequently apportioned into several subsamples which are distributed into a plurality of reaction chambers (reagent areas) to react with a reagent therein and to be analyzed after the reaction. Biological samples analyzed herein may be obtained from any biological sample including humans or any other mammal, birds, fish, reptiles, amphibians, insects, crustaceans, marine animals, plants, fungi, and microorganisms. The reacted sample will be assayed for the substance, or analyte of interest.

The fluid sample may be assessed for contamination microoganisms such as *E. coli, Pseudomonas* sp., *H. pylori, Streptococcus* sp., *Chlamydia* and mononucleosis pathogens. Metals which may be detected include, but are not limited to, iron, manganese, sodium, potassium, lithium, calcium, and magnesium.

In many applications, it is desired to measure a color, light or wavelength emission developed by the reaction of reagents with the sample fluid and which may be measured or detected by analyzers known to those of ordinary skill in the art. It is also feasible to make electrical measurements of the sample, using electrodes positioned in the small wells in the chip. Examples of such analyses include electrochemical signal transducers based on amperometric, impedimetric, or potentimetric detection methods. Examples include the detection of oxidative and reductive chemistries and the detection of binding events.

It is contemplated that virtually any reagent used in the fields of biological, chemical, or biochemical analyses could be used in the microfluidic distributing devices of the presently claimed and disclosed inventive concepts. Reagents may undergo changes whereby the intensity, nature, frequency, or type of the signal generated is proportional to the concentration of the analyte measured in the clinical specimen. These reagents may contain indicator dyes, metals, enzymes, polymers, antibodies, electrochemically reactive ingredients and various other chemicals placed onto carriers (also referred to herein as reagent substrates). Carriers often used are papers, membranes or polymers with various sample uptake and transport properties. Liquid reagents, when used, are preferably isolated by barrier materials which prevent migration of water throughout the device, thus avoiding changes in the concentration through transpiration or evaporation and preventing moisture from reaching the dry reagents.

Any method of detecting and measuring an analyte in a liquid sample can be used in the microfluidic devices of the presently claimed and disclosed inventive concepts. A variety of assays for detecting analytes are well known in the art and include, for example, enzyme inhibition assays, antibody stains, latex agglutination, and immunoassays, e.g., radioimmunoassay. The term "antibody" herein is used in the broadest sense and refers to, for example, intact monoclonal antibodies, polyclonal antibodies, multispecific antibodies (e.g., bispecific antibodies), and to antibody fragments that exhibit the desired biological activity (e.g., antigen-binding). The antibody can be of any type or class (e.g., IgG, IgE, IgM, IgD, and IgA) or sub-class (e.g., IgG1, IgG2, IgG3, IgG4, IgA1 and IgA2).

Immunoassays as noted, including radioimmunoassay and enzyme-linked immunoassays, are useful in the methods of the presently claimed and disclosed inventive concepts. A variety of immunoassay formats, including, for example, competitive and non-competitive immunoassay formats, antigen capture assays and two-antibody sandwich assays can be used in the methods of the invention. Enzyme-linked immunosorbent assays (ELISAs) can be used in the presently claimed and disclosed inventive concepts. In the case of an enzyme immunoassay, an enzyme is typically conjugated to the second antibody, generally by means of glutaraldehyde or periodate. As will be readily recognized, however, a wide variety of different conjugation techniques exist which are readily available to one skilled in the art.

In certain embodiments, the analytes are detected and measured using chemiluminescent detection. For example, in certain embodiments, analyte-specific antibodies are used to capture an analyte present in the biological sample and an antibody specific for the specific antibodies and labeled with an chemiluminescent label is used to detect the analyte present in the sample. Any chemiluminescent label and detection system can be used in the present devices and methods. Chemiluminescent secondary antibodies can be obtained commercially from various sources. Methods of detecting chemiluminescent secondary antibodies are known in the art and are not further discussed herein in detail.

Examples of assays that may be carried out during the use of the microfluidic distributing devices described herein include, but are not limited to, tests for blood gases, clotting factors, immunogens, bacteria, and proteins. In one embodiment the assays that may be detected with the test device is a "luminescent $O_2$ channel assay" (LOCK)) which includes the use of for example, Sandwich Assays based on an analyte-specific antibody and a biotinylated antibody wherein specific wavelengths are generated by the fluid subsample and detected by the test device. Reagent configurations for the assay method include for example Sandwich Formats based on an antigen or an antibody, a Competitive Format, or a Sandwich Format with Extended Linker and may be used in immunoassays, infectious disease testing, and DNA testing. Specific blood chemicals which may be measured include, but are not limited to, TSH, free T4, free T3, Total PSA, free PSA, AFP, CEA, CA15.3, CA 19-9, CA 125, Cardiac Troponin-I, NT-pro BNP, myoglobin, mass CKMB (MMB), BNP, Ferritin, Vitamin $B_{12}$, Folate, total B-HCG, FSH, LH, prolactin, estradiol, testosterone, progesterone, and digoxin.

Fluorescent detection also can be useful for detecting analytes in the presently claimed and disclosed inventive concepts. Useful fluorochromes include, but are not limited to, DAPI, fluorescein, lanthanide metals, Hoechst 33258, R-phycocyanin, B-phycoerythrin, R-phycoerythrin, rhodamine, Texas red and lissamine. Fluorescent compounds, can be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic color visually detectable with a light microscope. Radioimmunoassays (RIAs) can be useful in certain methods of the invention. Such assays are well known in the art. Radioimmunoassays can be performed, for example, with $^{125}$I-labeled primary or secondary antibody.

Separation steps are possible in which an analyte is reacted with reagent in a first reaction chamber and then the reacted reagent or sample is directed to a second reaction chamber for further reaction. In addition, a reagent can be re-suspended in a first reaction chamber and moved to a second reaction chamber for a reaction. An analyte or reagent can be trapped in a first or second chamber and a determination made of free versus bound reagent. The determination of a free versus bound reagent is particularly useful for multizone immunoassay and nucleic acid assays. There are various types of multizone immunoassays that could be adapted to this device. In the case of adaption of immunochromatography assays, reagent filters are placed into separate wells and do not have to be in physical contact as chromatographic forces are not in play. Immunoassays or DNA assay can be developed for detection of bacteria such as Gram negative species (e.g., *E. coli, Enterobacter, Pseudomonas, Klebsiella*) and Gram positive species (e.g., *Staphylococcus aureus, Enterococcus*). Immunoassays can be developed for complete panels of proteins and peptides such as albumin, hemoglobin, myoglobulin, α-1-microglobulin, immunoglobulins, enzymes, glycoproteins, protease inhibitors, drugs and cytokines. The device may be used in analysis of urine for one or more components therein or aspects thereof, such as, but not limited to, leukocytes, nitrites, urobilinogen, proteins, albumin, creatinine, uristatin, calcium oxalate, myoglobin, pH, blood, specific gravity, ketone, bilirubin and glucose.

Figure 1:
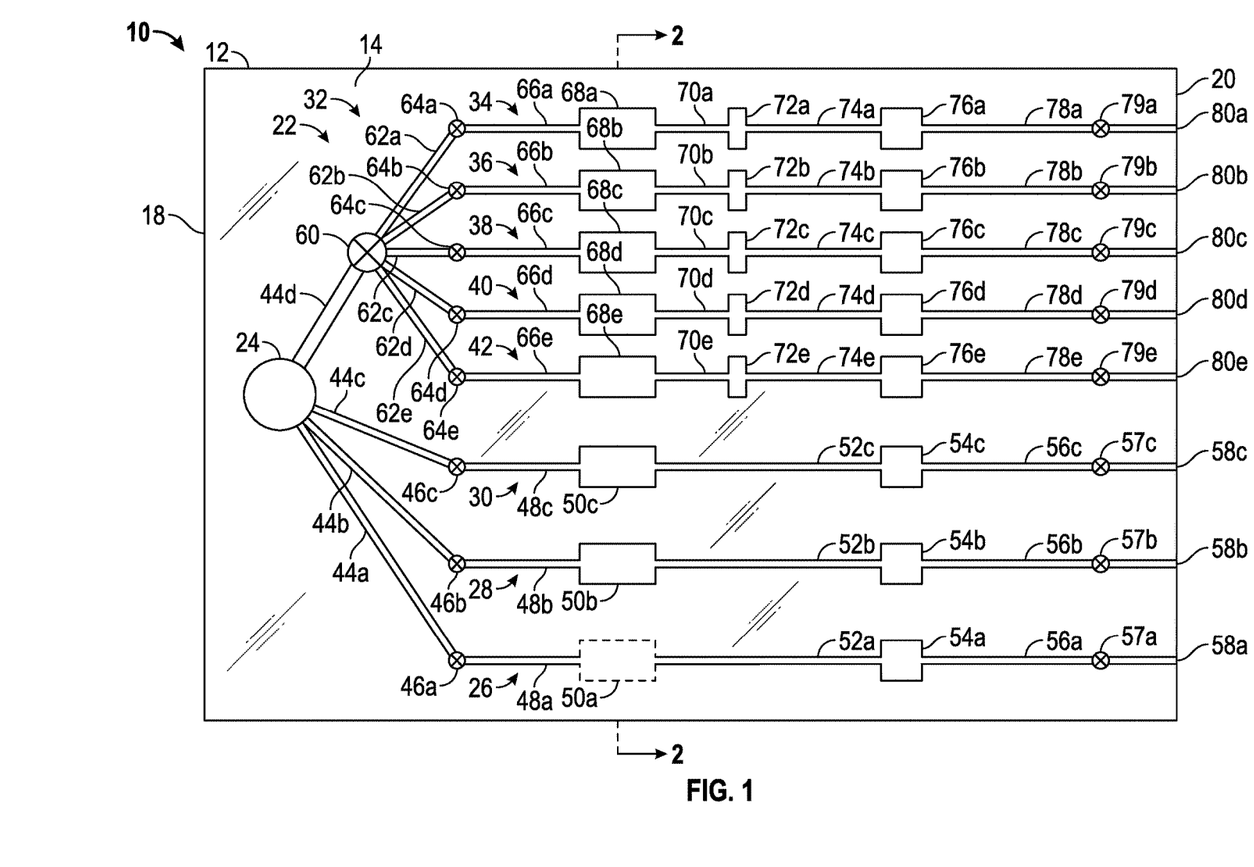
FIG. 1 is a top plan view of an embodiment of a microfluidic distributing device constructed in accordance with the inventive concepts disclosed herein.
Figure 2:
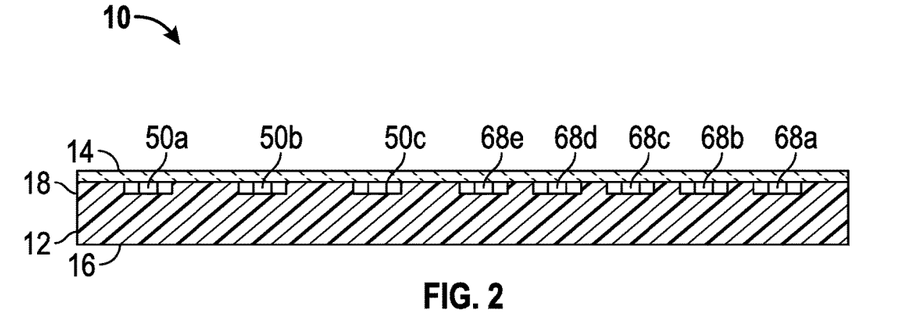
FIG. 2 is a sectional view taken along line 2-2 of FIG. 1.

Referring now to the drawings, and more particularly to FIGS. 1 and 2, shown therein is an exemplary embodiment of a microfluidic distributing device 10 constructed in accordance with the inventive concepts disclosed and claimed herein. The microfluidic distributing device 10 comprises a base portion 12 and a lid or top cover 14. The base portion 12 has a bottom 16, an outer peripheral edge 18 which forms a perimeter, and an exit port edge 20. Formed into the microfluidic distributing device 10 is a microfluidic channel system 22. The microfluidic channel system 22 has a fluid sample entry port 24 in the base 12 for receiving a fluid sample from a fluid container (not shown) engaged with the microfluidic distributing device 10.

The microfluidic distributing device 10 may be referred to as a "chip." The microfluidic distributing device 10 is generally small and flat, having a shape and dimensions as discussed elsewhere herein. The microfluidic distributing device 10 is shown as having a rectangular shape, however it will be understood that the shapes of the microfluidic distributing devices of the presently claimed and disclosed inventive concepts, include but are not limited to, round, rectangular, trapezoidal, irregular, oval, star, or any other geometric shape which allows the microfluidic passageways therein to function in accordance with the presently claimed and disclosed inventive concepts. It will be appreciated that there are several ways in which the various components of the microfluidic channel system 22 can be formed in the base portion 12, such as, but not limited to, injection molding, laser ablation, diamond milling, embossing, and combinations thereof, for example.

The top cover 14 has an opening or area of weakness above the fluid sample entry port 24 in the base 12. The top cover 14 may be transparent to allow for imaging and observation of the fluid sample as it is passed through the microfluidic channel system 22. The top cover 14 may be secured (permanently or detachably) to the base portion 12 in any suitable manner such as by molding, ultrasonic welding, radiofrequency welding, bonding, gluing, double-sided adhesive tapes, and combinations thereof, for example, provided that a substantially fluid-impermeable connection is formed between the base portion 12 and the top cover 14 of the microfluidic distributing device 10.

The microfluidic distributing device 10 may be reusable or disposable depending on the intended use. In one embodiment, the microfluidic distributing device 10 may be disposed of after a single use. The microfluidic distributing device 10 is generally made of inexpensive materials to the extent possible, while being compatible with the reagents and the samples which are to be analyzed. By way of example, the microfluidic distributing device 10 may be made of plastics, such as polycarbonate, polystyrene, polyacrylates, or polyurethene, or other materials, such as silicates, silicone, ceramics, glass, wax, resins, metals, and combinations thereof but is not limited to such materials. Other materials which may be used are described elsewhere herein.

In the non-limiting embodiment of the presently disclosed and claimed inventive concepts shown in FIGS. 1 and 2, the microfluidic channel system 22 comprises a plurality of microchannels into which fluid samples are introduced and analyzed. The microfluidic channel system 22 of FIGS. 1A and 1B includes a microchannel 26, a second microchannel 28, a third microchannel 30, and a fourth microchannel 32. The first microchannel 26 is intended, for example, to be used to hemolyze a blood sample and to analyze the hemolysate. The second microchannel 28 is intended, for example, to be used to analyze a whole blood sample. The third microchannel 30 may be used for an alternative analysis. The microfluidic channel system 22 further comprises a fourth microchannel 32 which comprises a plurality of submicrochannels 34, 36, 38, 40, and 42 which treat subsamples of a blood sample applied to the microfluidic distributing device 10. It will be understood that in other embodiments of the microfluidic distributing device of the presently disclosed and claimed inventive concept(s), the device may contain less or more than four microchannels, such as one, two, three, five, six, seven, eight, nine, or ten or more microchannels, and less than or more than one microchannel which comprises submicrochannels, such as zero, two, three, or four, or more, or any combination thereof. Each of the microchannels 26, 28, 30, and 32 has a treatment sample apportionment channel 44*a*, 44*b*, 44*c*, and 44*d*, respectively, which is connected to and in fluid communication with the fluid sample entry port 24. More particularly, treatment sample apportionment channels 44*a*-44*d* receive portions of the fluid sample which is introduced into the fluid sample entry port 24. In other embodiments each microchannel 26, 28, 30, and 32 may be supplied with its own fluid sample entry port.

Regarding the microchannels 26, 28, and 30, the portions of the fluid sample received by treatment sample apportionment channels 44a-44c are delivered to valves 46a-46c, of the microchannels 26-30, respectively. In turn, valves 46a-46c are in fluid communication with valve exit channels 48a-48c which are in turn connected to and in fluid communication with reagent areas 50a-50c. The valves 46a-46c may be constructed so as to prevent backflow of a sample after it has passed therethrough. As used herein, "valve" means a device that may be controlled or actuated to control or regulate fluid, gas or solution flow between and among various components of the microfluidic device, including flow between flow channels, solvent or reagent reservoirs, reaction chamber, columns, manifold, temperature controlling elements and devices, and the like. By the way of example, and not by limitation, such valves may include mechanical (or micromechanical valves), (pressure activated) elastomeric valves, pneumatic valves, and solid-state valves. Examples of such valves and their method of fabrication may be found, for example, in "The New Generation of Microvalves" Analytical Chemistry, Felton, 429-432 (2003).

The fluid sample portions received by valves 46a-46c are thus passed through valve exit channels 48a-48c, to reagent areas 50a-50c, respectively, where the portions of the fluid samples are reacted with one or more reagents in the reagent areas 50a-50c. A single reagent area of the device may contain multiple reagents. Each reagent area 50a-50c generally contains one or more reagents which are reacted with the fluid sample which flows thereinto. Mixing of the fluid sample portion with the reagent may also occur in the reagent area. As used herein, the term "reagent area" may refer to more than one discrete chamber which contains a reagent. For example, a reagent area may comprise two separate reagent sub-chambers such that the fluid sample enters the first reagent sub-chamber where it reacts with a first reagent then is passed to a second reagent sub-chamber where the reacted fluid sample further reacts with a second reagent in the second reagent sub-chamber. After the fluid samples have been reacted in reagent areas 50a-50c, they are passed into reagent area exit channels 52a-52c, respectively. These reagent area exit channels 52a-52c are connected to and in fluid communication with metering areas 54a-54c, respectively. The fluid samples pass into the metering area 54a-54c where specifically measured portions of the fluid sample are passed into output channels 56a-56c, respectively, and out through exit ports 58a-58c, respectively, where the reacted and metered fluid samples may be delivered to test devices (FIGS. 3-7), which are able to analyze the reacted fluid samples which have exited through the exit ports 58a-58c. Each output channel 56a-56c optionally includes a closure valve 57a-57c, respectively, for enabling the corresponding output channel 56a-56c to be closed. For example, the closure valves 57a-57c may be actuated to close the output channels 56a-56c after samples have been treated in the microfluidic distributing device 10 but before the device 10 has been attached to a test device for analyzing the treated sample. As discussed elsewhere herein, the reagents in the reagent areas 50a-50c may be disposed on or in a substrate or on an inner surface of the reagent area 50a-50c. In alternative embodiments, reagents may be deposited on a surface of any one or more of apportionment channels 44a-44c, valve exit channels 48a-48c, reagent area exit channels 52a-52c, and output channels 56a-56c, where such a reagent would serve a useful purpose in accordance with the presently disclosed and claimed inventive concepts such as to provide an anticoagulant to prevent coagulation of a blood sample passing through the assay path. Reagent area 50a is shown in phantom to represent that reagent area 50a may or may not be present as a discrete entity.

The portion of the fluid sample received by apportionment channel 44d is delivered to a valve 60 for further apportionment and distribution of the fluid sample into the submicrochannels 34-42 of the microchannel 32 (the apportionment channel 44d may also be referred to herein as a main microchannel). More particularly, in the embodiment of FIGS. 1 and 2, as noted above, the microchannel 32 has five separate submicrochannels 34-42 for processing subsamples of the fluid sample held by the valve 60. Each submicrochannel 34-42 begins with a corresponding subapportionment channel 62a-62e, respectively, which extends from and is in fluid communication with the valve 60 and which is connected to and in fluid communication with a corresponding valve 64a-64e, respectively, which controls the flow (particularly inhibiting backflow) of the subsample into a corresponding reagent area 68a-68e via a corresponding valve exit channel 66a-66e, respectively.

The reagent areas 68a-68e are similar in nature to the reagent areas 50a-50c described above but generally contain different reagents. For example, in the embodiment of FIGS. 1 and 2, the reagents in reagent areas 68a-68e may be anticoagulants such as EDTA, NaF, heparin, oxalate, citrate, or any other substance known by persons have ordinary skill in the art of blood or plasma analysis. Each fluid subsample, once having been treated with the corresponding reagent is transported to a cell (e.g., blood cell) separation area 72a-72e, respectively, via a reagent area exit channel 70a-70e, which is in fluid communication with the corresponding reagent area 68a-68e and with the respective cell separation area 72a-72e. At the cell separation area 72a-72e, the cells are separated from the fluid (e.g., blood cells separated from plasma) which enables more efficient and accurate measurement of the desired aspect of the purified fluid (e.g., plasma) by a test device. The cell separation mechanism in the cell separation areas may be any feature, mechanism, device, or process by which blood cells are separated from plasma including, but not limited to, centrifugation, asymmetric membranes, tangential flow membranes, ultrasound, microfluidics, agglutination, adhesion, other physical blockage elements, or any combination of the above.

After separation from the cells, the treated fluid portion of the subsample is transferred to a corresponding metering area 76a-76e via a separation area exit channel 74a-74e which is in fluid communication with the corresponding cell separation area 72a-72e. Once in the metering area 76a-76e, each treated fluid (e.g., plasma) portion is metered into a specifically measured portion which is passed to a corresponding exit port 80a-80e via an output channel 78a-78e which is connected to, and in fluid communication with, the corresponding metering area 76a-76e and exit port 80a-80e. It is to be noted that one or more of the metering areas 54a-54c and 76a-76e may optionally be omitted from the corresponding microchannel or submicrochannel if such is not necessary for the microchannel to function in accordance with the presently disclosed and claimed inventive concepts, for example, if the entire subsample leaving the reagent area 50a-50c or 68a-68e is to be analyzed. Each output channel 78a-78c optionally includes a closure valve 79a-79c, respectively, for enabling the corresponding output channel to be closed. For example, the closure valves 79a-79c may be actuated to close the output channels 78a-78c after samples have been treated in the microfluidic distributing device 10 but before the device 10 has been attached to a test device for analyzing the treated sample.

Figure 3:
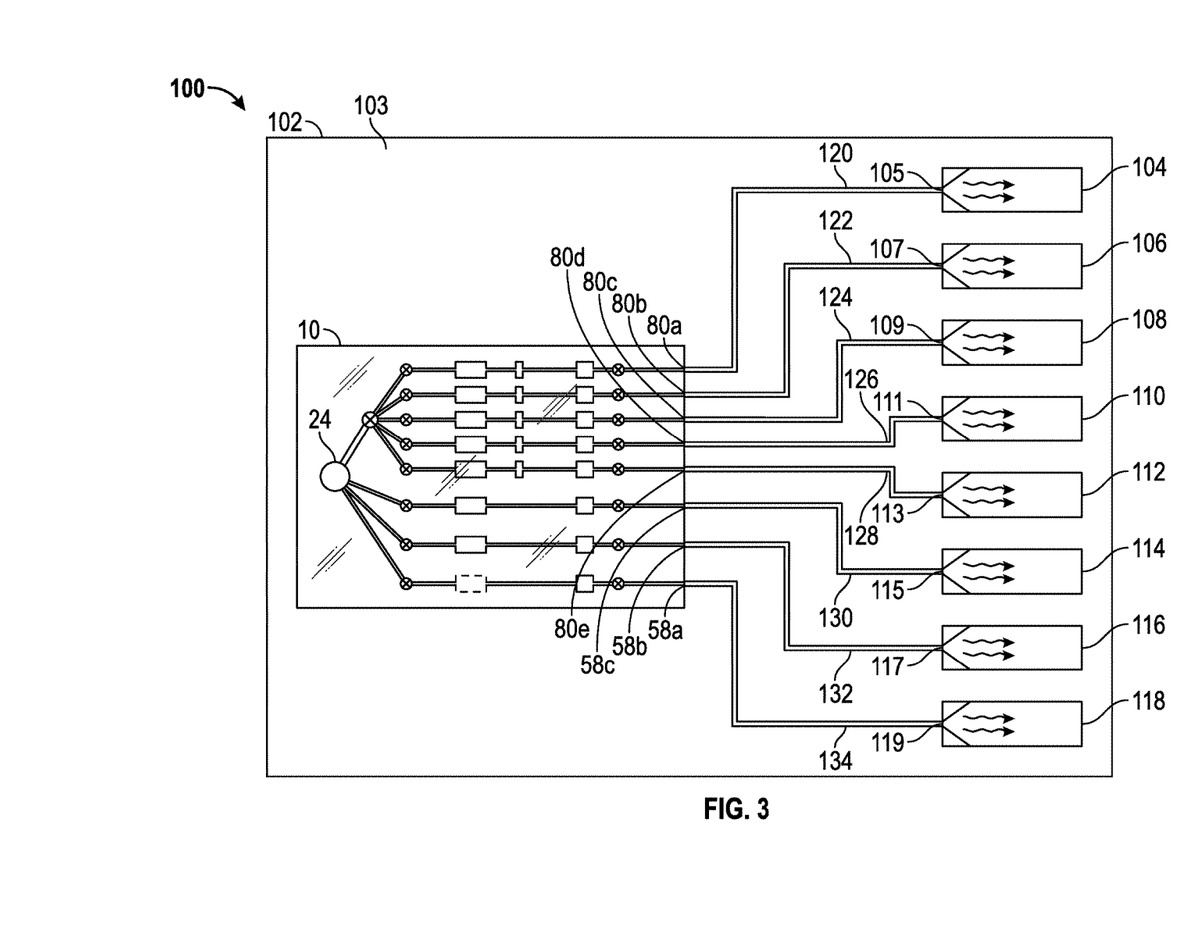
FIG. 3 is a schematic top plan view of a microfluidic analysis system constructed in accordance with the presently disclosed and claimed inventive concepts which employs a microfluidic distributing device as shown in FIG. 1.

Shown in FIG. 3 and designated therein by the general reference numeral 100 is a microfluidic analysis system constructed in accordance with the presently disclosed and claimed inventive concepts. The microfluidic analysis system 100 comprises a base 102 having an upper surface 103. A plurality of test devices designated by the general reference numerals 104, 106, 108, 110, 112, 114, 116, and 118, are positioned upon the upper surface 103 of the base 102. Each test device 104-118 has an entry port 105, 107, 109, 111, 113, 115, 117, and 119, respectively. Generally, each test device 104-118 is secured to the base 102 either frictionally or by insertion or by other securing mechanisms well known to persons of ordinary skill in the art, such as, but not limited to, snaps, fasteners, ridges, and tabs.

A microfluidic distributing device 10, as described previously, is disposed on the base 102, and as with the test devices 104-118, is usually secured to the base 102 either frictionally (for example by insertion into a cavity in the base 102) or by other securing mechanisms known in the art, for example as described above (although reference in the embodiment of FIG. 3 and other analysis systems below is made to the use of the microfluidic distributing device 10, it is intended that any microfluidic distributing device described and/or contemplated herein or which function in accordance with the presently disclosed and claimed inventive concepts may be used in a microfluidic analysis systems described herein). The base 102 further comprises a plurality of transfer conduits 120, 122, 124, 126, 128, 130, 132, and 134. As explained below, each transfer conduit 120-134 is positioned so as to be connected to one of the exit ports of the microfluidic distributing device 10 at one end of the corresponding transfer conduit, and with a corresponding entry port of the test device at the other end of the corresponding transfer conduit. For example, in the case of the embodiment of FIG. 3, exit port 80a is fluidly connected to entry port 105 of test device 104 by transfer conduit 120, exit port 80b is fluidly connected to entry port 107 of test device 106 by transfer conduit 122, exit port 80c is fluidly connected to entry port 109 of test device 108 by transfer conduit 124, exit port 80d is fluidly connected to entry port 111 of test device 110 by transfer conduit 126, exit port 80e is fluidly connected to entry port 113 of test device 112 by transfer conduit 128, exit port 58c is fluidly connected to entry port 115 of test device 114 by transfer conduit 130, exit port 58b is fluidly connected to entry port 117 of test device 116 by transfer conduit 132, and exit port 58a is fluidly connected to entry port 119 of test device 118. Thus, upon actuation of the microfluidic processes of the microfluidic distributing device 10, the fluid subsamples in the microchannels thereof can be transferred via the transfer conduits 120-134 to the test devices 104-118, respectively, for testing of the fluid subsamples in accordance with the desired analyses thereof. The transfer of the fluid subsamples into the test devices 104-118 and analyses therein of the fluid samples can occur simultaneously or independently, or sequentially, in accordance with the desired analyses.

Further, the microfluidic distributing device 10 can be disposed upon or otherwise attached to the base 102 before a fluid sample is disposed within the entry port 24 of microfluidic distributing device 10, or after a fluid sample is disposed within the entry port 24. Also, the microfluidic distributing device 10 can be activated to process the fluid sample before the microfluidic distributing device 10 is placed on the base 102, or after the microfluidic distributing device 10 is placed on the base 102.

Figure 4:
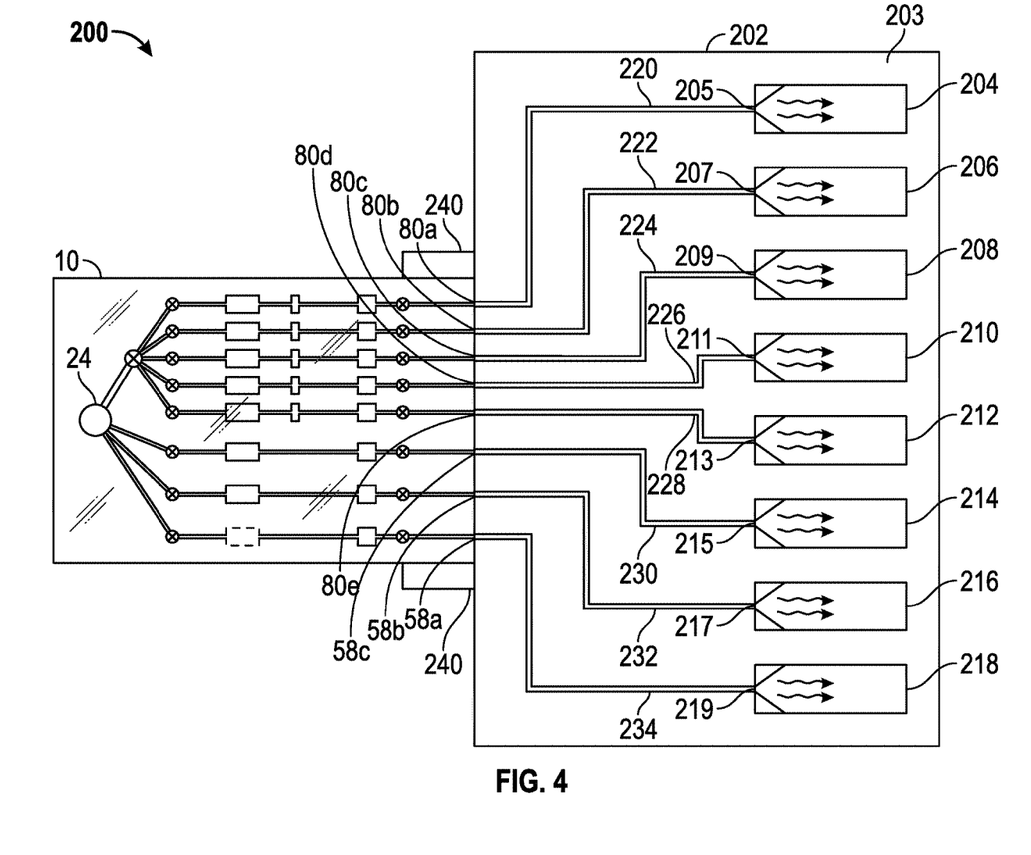
FIG. 4 is a schematic top plan view of another embodiment of a microfluidic analysis system constructed in accordance with the presently disclosed and claimed inventive concepts which employs a microfluidic distributing device as shown in FIG. 1.

Shown in FIG. 4 and designated therein by the general reference numeral 200 is another microfluidic analysis system constructed in accordance with the presently disclosed and claimed inventive concepts. The microfluidic analysis system 200 is similar in many respects to the microfluidic analysis system 100 of FIG. 3 except for the manner in which the microfluidic distributing device 10 is secured for testing. The microfluidic analysis system 200 comprises a base 202 having an upper surface 203. A plurality of test devices designated by the general reference numerals 204, 206, 208, 210, 212, 214, 216, and 218, are positioned upon the upper surface 203 of the base 202. Each test device 204-218 has an entry port 205, 207, 209, 211, 213, 215, 217, and 219, respectively. Generally, each test device 204-218 is secured to the base 202 either frictionally or by insertion or by other securing mechanisms well known to persons of ordinary skill in the art, such as, but not limited to, snaps, fasteners, ridges, and tabs.

A microfluidic distributing device 10, as described previously, is attached to the base 202 by insertion into an engaging mechanism 240 such that the device 10 is securely connected (removably or non-removably) to the base 202. The engaging mechanism 240 may be any suitable mechanism known in the art. The base 202 further comprises a plurality of transfer conduits 220, 222, 224, 226, 228, 230, 232, and 234. As explained below, each transfer conduit 220-234 is positioned so as to connect with one of the exit ports of the microfluidic distributing device 10 at one end of the corresponding transfer conduit, and with a corresponding entry port of the test device at the other end of the corresponding transfer conduit. In the case of the embodiment of FIG. 4, exit port 80a is fluidly connected to entry port 205 of test device 204 by transfer conduit 220, exit port 80b is fluidly connected to entry port 207 of test device 206 by transfer conduit 222, exit port 80c is fluidly connected to entry port 209 of test device 208 by transfer conduit 224, exit port 80d is fluidly connected to entry port 211 of test device 210 by transfer conduit 226, exit port 80e is fluidly connected to entry port 213 of test device 212 by transfer conduit 228, exit port 58c is fluidly connected to entry port 215 of test device 214 by transfer conduit 230, exit port 58b is fluidly connected to entry port 217 of test device 216 by transfer conduit 232, and exit port 58a is fluidly connected to entry port 219 of test device 218. Thus, upon actuation of the microfluidic processes of the microfluidic distributing device 10, the fluid subsamples in the microchannels thereof can be transferred via the transfer conduits 220-234 to the test devices 204-218, respectively, for testing of the fluid subsamples in accordance with the desired analyses thereof. The transfer of the fluid subsamples into the test devices 204-218 and analyses therein of the fluid samples can occur simultaneously or independently, or sequentially, in accordance with the desired analyses.

Further, the microfluidic distributing device 10 can be disposed upon or otherwise attached to the base 202 before a fluid sample is disposed within the entry port 24 of microfluidic distributing device 10, or after a fluid sample is disposed within the entry port 24. Also, the microfluidic distributing device 10 can be activated to process the fluid sample before the microfluidic distributing device 10 is attached to the base 202, or after the microfluidic distributing device 10 is attached to the base 202.

Figure 5:
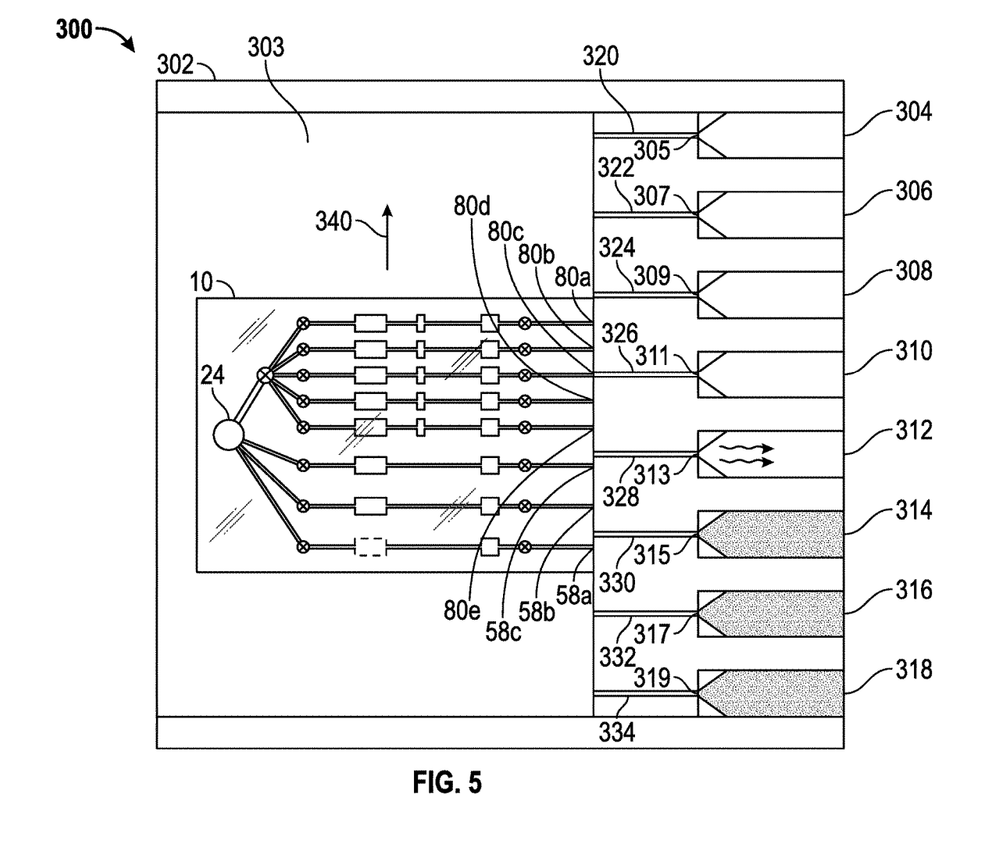
FIG. 5 is a schematic top plan view of another embodiment of a microfluidic analysis system constructed in accordance with the presently disclosed and claimed inventive concepts which employs a microfluidic distributing device as shown in FIG. 1.

Shown in FIG. 5 and designated therein by the general reference numeral 300 is a microfluidic analysis system constructed in accordance with the presently disclosed and claimed inventive concepts. The microfluidic analysis system 300 is similar in many respects to the microfluidic analysis system 100 of FIG. 3 except for the manner in which the microfluidic distributing device 10 is secured to the base and how the exit ports of the microfluidic distributing device 10 are aligned with the test devices. More particularly, the microfluidic analysis system 300 comprises a base 302 having an upper surface 303. A plurality of test devices designated by the general reference numerals 304, 306, 308, 310, 312, 314, 316, and 318, are positioned upon the upper surface 303 of the base 302. Each test device 304-318 has an entry port 305, 307, 309, 311, 313, 315, 317, and 319, respectively. Generally, each test device 304-318 is secured to the base 302 either frictionally or by other securing mechanisms well known to persons of ordinary skill in the art, such as, but not limited to, snaps, fasteners, ridges, and tabs.

A microfluidic distributing device 10, as described previously, is movably disposed on the base 302, such that the microfluidic distributing device 10 can be shifted manually or automatically, in a direction 340 (or the reverse), such that the exit ports 80*a*-80*e* and 58*c*-58*a* can be aligned with the corresponding entry ports 305-319 of test devices 302-318 by moving the microfluidic distributing device 10 on the base 302. The base 302 further comprises a plurality of transfer conduits 320, 322, 324, 326, 328, 330, 332, and 334. Each transfer conduit 320-334 is positioned so as to connect with one of the exit ports of the microfluidic distributing device 10 at one end of the corresponding transfer conduit, and with a corresponding entry port of the test device at the other end of the corresponding transfer conduit. In the case of the embodiment of FIG. 5, exit port 80*a* is fluidly connectable to entry port 305 of test device 304 by transfer conduit 320, exit port 80*b* is fluidly connectable to entry port 207 of test device 206 by transfer conduit 322, exit port 80*c* is fluidly connectable to entry port 309 of test device 308 by transfer conduit 324, exit port 80*d* is fluidly connectable to entry port 311 of test device 310 by transfer conduit 326, exit port 80*e* is fluidly connectable to entry port 313 of test device 312 by transfer conduit 328, exit port 58*c* is fluidly connectable to entry port 315 of test device 314 by transfer conduit 330, exit port 58*b* is fluidly connectable to entry port 317 of test device 316 by transfer conduit 332, and exit port 58*a* is fluidly connectable to entry port 319 of test device 318. Thus, upon actuation of the microfluidic processes of the microfluidic distributing device 10, the fluid subsamples in the microchannels thereof can be transferred via the transfer conduits 320-334 to the test devices 304-318, respectively, for testing of the fluid subsamples in accordance with the desired analyses thereof. The transfer of the fluid subsamples can occur serially or non-serially in accordance with the desired analyses.

Further, the microfluidic distributing device 10 can be disposed upon or otherwise attached to the base 302 before a fluid sample is disposed within the entry port 24 of microfluidic distributing device 10, or after a fluid sample is disposed within the entry port 24. Also, the microfluidic distributing device 10 can be activated to process the fluid sample before the microfluidic distributing device 10 is placed on the base 302, or after the microfluidic distributing device 10 is placed on the base 302.

Figure 6:
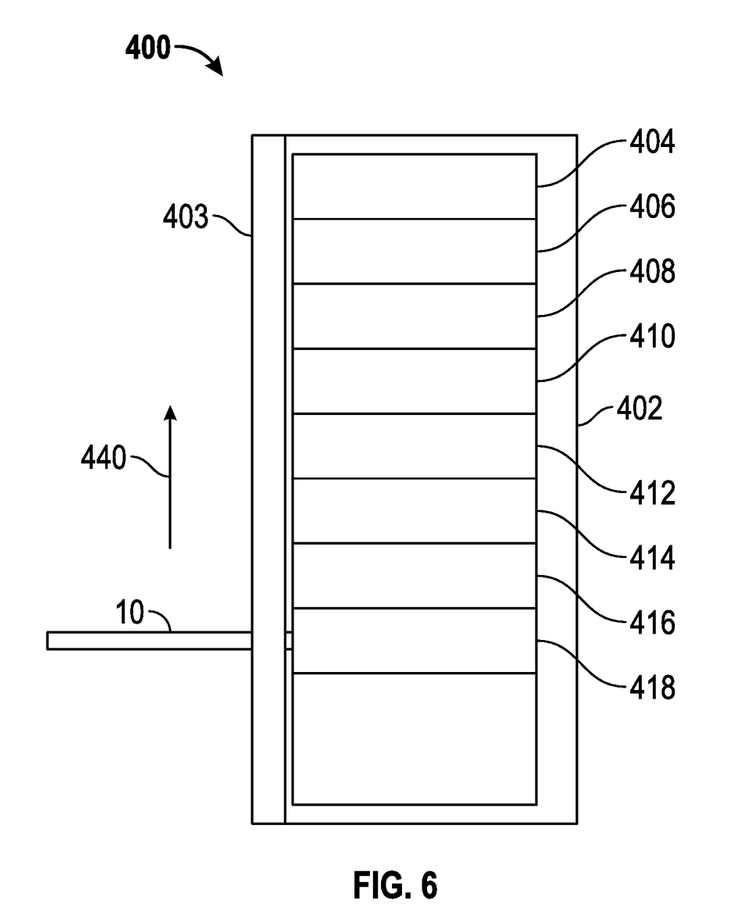
FIG. 6 is a schematic side elevational view of another embodiment of a microfluidic analysis system constructed in accordance with the presently disclosed and claimed inventive concepts which employs a microfluidic distributing device as shown in FIG. 1.

Shown in FIG. 6 and designated therein by the general reference numeral 400 is another embodiment of a microfluidic analysis system constructed in accordance with the presently disclosed and claimed inventive concepts. The microfluidic analysis system 400 comprises a base 402 having a plurality of test devices designated by the general reference numerals 404, 406, 408, 410, 412, 414, 416, and 418, which are positioned vertically in the base 402. Each test device 404-418 has an entry port (not shown) which is similar to the entry ports of the test devices 104-118. The test device 404-418 may be secured in the base 402 either frictionally or by other securing mechanisms well known to persons of ordinary skill in the art, such as, but not limited to, snaps, fasteners, ridges, and tabs. The base 402 further comprises a microfluidic device holder 403 which includes a track, rail, or other suitable mechanism which enables a microfluidic distributing device of the presently disclosed and claimed inventive concepts (such as microfluidic distributing device 10) to be shifted vertically in direction 440, or downwardly in relation to the orientation of the test devices 404-418.

A microfluidic distributing device 10, as described previously, is positioned within the microfluidic device holder 403 whereby the microfluidic distributing device 10 may be shifted up or down for transferring a fluidic sample into the test devices 404-418 serially. The base 402 further comprises a plurality of transfer conduits (not shown) wherein each exit port of the microfluidic distributing device 10 can be placed in fluid communication with a corresponding transfer conduit which is in fluid communication with an entry port of a corresponding test device. The fluidic connections are not shown in the embodiment of FIG. 6, but are intended to be similar to those shown, for example, in the microfluidic analysis system 300 of FIG. 5. Thus, upon actuation of the microfluidic processes of the microfluidic distributing device 10, the fluid subsamples in the microchannels thereof therein can be transferred via transfer conduits to the test devices 404-418, respectively, for testing of the fluid subsamples in accordance with the desired analyses thereof. The transfer of the fluid subsamples generally occurs serially, consecutively, or non-consecutively.

Further, the microfluidic distributing device 10 can be inserted into or otherwise attached to the microfluidic device holder 403 before a fluid sample is disposed within the entry port 24 of microfluidic distributing device 10, or after a fluid sample is disposed within the entry port 24. Also, the microfluidic distributing device 10 can be activated to process the fluid sample before the microfluidic distributing device 10 is placed in the microfluidic device holder 403, or after the microfluidic distributing device 10 is placed on the microfluidic device holder 403.

Figure 7:
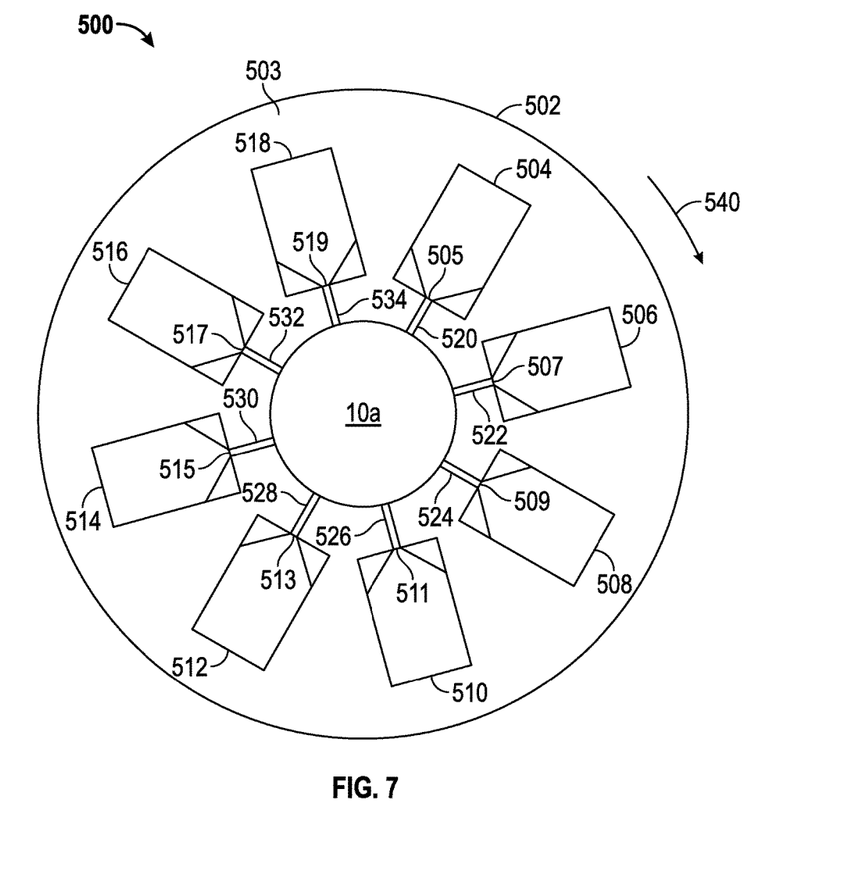
FIG. 7 is a schematic top plan view of another embodiment of a microfluidic analysis system for use with an alternate microfluidic distributing device and constructed in accordance with the presently disclosed and claimed inventive concepts.

Shown in FIG. 7 and designated therein by the general reference numeral 500 is another embodiment of a microfluidic analysis system constructed in accordance with the presently disclosed and claimed inventive concepts. Operation of the microfluidic analysis system 500 is substantially similar to that of system 100, except for the shape of the components thereof. The microfluidic analysis system 500 comprises a disk-shaped base 502 having an upper surface 503. A plurality of test devices designated by the general reference numerals 504, 506, 508, 510, 512, 514, 516, and 518, are positioned radially upon the upper surface 503 of the base 502. Each test device 504-518 has an entry port 505, 507, 509, 511, 513, 515, 517, and 519, respectively. Generally each test device 504-518 is secured to the base 500 either frictionally or by other securing mechanisms well known to persons of ordinary skill in the art, such as, but not limited to, snaps, fasteners, ridges, and tabs as discussed above.

A microfluidic distributing device 10*a* having a microfluidic channel system, and similar to microfluidic distributing device 10, as described previously except having a disk-shape, is disposed on the base 502, and as with the test devices 504-518, is usually secured to the base 502 either frictionally (for example by insertion into a cavity in the base 502) or by other securing mechanisms known in the art, for example as described above. The base 502 further comprises a plurality of transfer conduits 520, 522, 524, 526, 528, 530, 532, and 534. Each transfer conduit 520-534 is positioned so as to connect with one of the exit ports (not shown, but similar to the exit ports of microfluidic distributing device 10) of the microfluidic distributing device 10a at one end of the corresponding transfer conduit, and with a corresponding entry port of the test device at the other end of the corresponding transfer conduit. In the case of the embodiment of FIG. 7, an exit port of microfluidic distributing device 10a is fluidly connected to entry port 505 of test device 504 by transfer conduit 520, an exit port of microfluidic distributing device 10a is fluidly connected to entry port 507 of test device 506 by transfer conduit 522, an exit port of microfluidic distributing device 10a is fluidly connected to entry port 509 of test device 508 by transfer conduit 524, an exit port of microfluidic distributing device 10a is fluidly connected to entry port 511 of test device 510 by transfer conduit 526, an exit port of microfluidic distributing device 10a is fluidly connected to entry port 513 of test device 512 by transfer conduit 528, an exit port of microfluidic distributing device 10a is fluidly connected to entry port 515 of test device 514 by transfer conduit 530, an exit port of microfluidic distributing device 10a is fluidly connected to entry port 517 of test device 516 by transfer conduit 532, and an exit port of microfluidic distributing device 10a is fluidly connected to entry port 519 of test device 518. Thus, upon actuation of the microfluidic processes of the microfluidic distributing device 10a, the fluid subsamples therein can be transferred via the transfer conduits 520-534 to the test devices 504-518, respectively, for testing of the fluid subsamples in accordance with the desired analyses thereof. The transfer of the fluid subsamples into the test devices 504-518 can occur simultaneously or independently, or sequentially, in accordance with the desired analyses. In one embodiment, the microfluidic distributing device 10a can be rotated to align the microfluidic distributing device 10a with the proper transfer conduits 520-534 on the base 502.

Further, the microfluidic distributing device 10a can be disposed upon or otherwise attached to the base 502 before a fluid sample is disposed within an entry port (not shown) thereof, or after a fluid sample is disposed within the said entry port. Also, the microfluidic distributing device 10a can be activated to process the fluid sample before the microfluidic distributing device 10a is placed on the base 502, or after the microfluidic distributing device 10a is placed on the base 502.

Fluid samples and subsamples thereof may be propelled into and through the microchannels of the microfluidic distributing devices described herein by passive or active fluidics including, but not limited to, capillary force, syringe pump, pistons, pneumatic, actuators, centrifugation, solenoids, linear actuators, peristaltic pump, electrophoresis, memory alloy valves, surface acoustic wave, or combinations of the above. Types of valves that may be used include, but are not limited to, check valves, on/off valves, memory alloy valves, solenoids, linear actuators, or any other valve which functions to control, stop, or start flow of the fluid samples.

The fluid samples and subsamples thereof may be mixed before, during, or after exposure to the reagents in the reagent areas. Mixing may be by passive or active mechanisms. For example, passive mechanisms include, but are not limited to, herring bone features, posts, or chevrons, and active mechanisms include, but are not limited to, piezo electric motors, surface acoustic wave means, centrifugal force, electrophoresis, and magnetic movement of particles, and combinations thereof.

Reagent areas as described herein, wherein the fluid samples may be held for mixing, reaction with reagents, or both, typically have a width in a range of, but not limited to, 0.5 mm to 3 mm, and have a depth in a range of, but not limited to, 0.2 mm to 3.0 mm, and have a length in a range of, but not limited to, 1 mm to 25 mm. Metering areas as described herein may have similar dimensions, but also may have greater lengths, depths, or widths depending on the volume of the fluid subsample desired to be exposed to the test devices used with the microfluidic distributing devices of the presently disclosed and claimed inventive concepts. The dimensions of the fluid sample entry port 24 are typically (but not limited to) in the range of 0.2 mm to 3.0 mm (depth) and 0.2 mm to 3.0 mm (diameter).

Reagents may be disposed or deposited in the reagent areas (or elsewhere in the microchannel) as dry powders, lyophilized spheres or granules, dried on a surface of the reagent area chamber, as liquids, for example, in pouches or blister packs, or on substrates as discussed elsewhere herein. In general, whole blood samples will need to be exposed to an anticoagulant (e.g., heparin) in the reagent area or in a portion of the microchannel upstream of the reagent area. Samples to be hemolyzed will generally require a surfactant or lysing agent (e.g., Saponin) in the reagent area or upstream thereof. In a microchannel designed to assay a whole blood sample which is to be hemolyzed, the microchannel may be absent a discrete reagent area such that the surfactant or lysing agent may simply be deposited in a channel between the valve and the exit port (or metering area, if present).

The microchannels described herein are shown generally as linear thereby allowing a substantially straight-line flow of fluid therethrough. It is to be understood, however, that the present inventive concepts are not limited to straight flow paths and may comprise curved, angled, or otherwise non-linear microchannel flow paths. It is to be further understood that a first portion of a microchannel may be straight, and a second portion of the same microchannel may be curved, angled, or otherwise non-linear.

The microfluidic distributing device of the presently disclosed and claimed inventive concepts may further include one or more sensors in fluidic communication with the microchannel for detecting some aspect of the subsample therein. Such sensors are well known in the art, and therefore no further discussion thereof is deemed necessary.

Although the presently claimed and disclosed inventive concepts and their advantages have been described in detail with reference to certain exemplary embodiments and implementations thereof, it should be understood that various changes, substitutions, alterations, modifications, and enhancements can be made to the presently claimed and disclosed inventive concepts described herein without departing from the spirit and scope of the presently claimed and disclosed inventive concepts as defined by the appended claims. Moreover, the scope of the presently claimed and disclosed inventive concepts is not intended to be limited to the particular embodiments of the processes, assemblies, items of manufacture, compositions of matter, means, methods and steps described in the specification. As one of ordinary skill in the art will readily appreciate from the present disclosure many equivalent processes, assemblies, items of manufacture, compositions of matter, means, methods, or steps, presently existing or later to be developed that perform substantially the same function or achieve substantially the same result as the corresponding embodiments described herein may be utilized according to the presently claimed and disclosed inventive concept(s) disclosed herein. Accordingly, the appended claims are intended to include within their scope all such equivalent processes, assemblies, items of manufacture, compositions of matter, means, methods, or steps. Furthermore, each of the references, patents or publications cited herein is hereby expressly incorporated by reference in its entirety.

The invention claimed is:

1. A method of treating a plurality of fluid subsamples, comprising:

introducing a fluid sample into a microfluidic analysis system, the microfluidic analysis system comprising a microfluidic distributing device and a plurality of test devices, wherein the fluid sample is introduced into a fluid sample entry port of the microfluidic distributing device, the microfluidic distributing device containing a base portion having the fluid sample entry port for receiving the fluid sample, a plurality of fluid flow microchannels in fluid communication with the fluid sample entry port such that the fluid sample received in the fluid sample entry port is separated into a plurality of fluid subsamples, and a plurality of fluid subsample exit ports, each of the fluid subsample exit ports in fluid communication with a corresponding one of the microchannels, wherein each of the microchannels has a valve disposed therein for controlling flow of the fluid subsample through the microchannel, and a reagent area with a reagent for reacting on or with the fluid subsample passing through the microchannel;

dividing the fluid sample into a plurality of fluid subsamples and distributing the fluid subsamples into the microchannels of the microfluidic distributing device to dispose a fluid subsample within each microchannel, wherein the fluid subsample is treated by reaction with the reagent in the reagent area of the microchannel to form a reacted fluid subsample and wherein at least a portion of the reacted fluid subsample is passed through the exit port of the microchannel into one of the plurality of test devices, wherein each of the plurality of test devices is in fluid communication with a separate exit port of the microfluidic distributing device to receive and analyze the fluid subsample received from the corresponding exit port and further wherein the plurality of test devices are arranged so that the microfluidic distributing device is moveable to selectively engage each of the plurality of test devices;

analyzing the reacted fluid subsample via selectively utilizing the plurality of test devices.

2. The method of claim 1, wherein at least one of the fluid subsamples is further subdivided before reaching the reagent area.

3. The method of claim 1, wherein each fluid subsample is treated with a different reagent.

4. The method of claim 3, wherein the fluid sample is a blood sample.

5. The method of claim 3, wherein at least one fluid subsample of the blood sample is hemolyzed.

6. The method of claim 3, wherein at least one fluid subsample of the blood sample is exposed to an anticoagulant and tested as a whole blood sample.

7. The method of claim 3, wherein at least one fluid subsample of the blood sample is treated to form plasma from the fluid subsample.

8. The method of claim 3, wherein the fluid subsample is coagulated to form a serum which is reacted with the reagent in the reagent area.

* * * * *